United States Patent [19]

Soga et al.

[11] 4,331,872
[45] May 25, 1982

[54] METHOD FOR MEASUREMENT OF DISTRIBUTION OF INCLUSIONS IN A SLAB BY ELECTRON BEAM IRRADIATION

[75] Inventors: Hiromu Soga; Koichi Kitamura, both of Kitakyushu; Tomio Sasaki, Tokyo; Mitsuyoshi Sato, Tokyo; Hiroshi Ishijima, Tokyo, all of Japan

[73] Assignees: Nippon Steel Corporation; Kabushiki Kaisha Daini Seikosha, both of Tokyo, Japan

[21] Appl. No.: 160,573

[22] Filed: Jun. 17, 1980

[30] Foreign Application Priority Data

Jun. 29, 1979 [JP] Japan .................................. 54-82831
Jun. 29, 1979 [JP] Japan .................................. 54-82832

[51] Int. Cl.$^3$ ............................................ G01N 23/00
[52] U.S. Cl. .................................... 250/307; 250/310; 250/399
[58] Field of Search ............... 250/307, 310, 396, 397, 250/398, 399

[56] References Cited

U.S. PATENT DOCUMENTS

| | | | |
|---|---|---|---|
| 3,193,679 | 7/1965 | Melford et al. | 250/310 |
| 3,374,349 | 3/1968 | Macres | 250/310 |
| 3,376,415 | 4/1968 | Krogstad et al. | 259/310 |
| 3,733,484 | 5/1973 | Bayard | 250/310 |
| 4,037,101 | 7/1977 | Okumura et al. | 250/307 |

*Primary Examiner*—Bruce C. Anderson
*Attorney, Agent, or Firm*—Wenderoth, Lind & Ponack

[57] ABSTRACT

In a method for the measurement of the distribution of the inclusions in a slab by electron beam irradiation, an electron beam of relatively large diameter is irradiated onto a relatively large specimen of the slab and a spectrum analysis of the characteristic X-rays is effected by using planar analyzing crystals, in order to obtain the data of the two-dimensional distribution of the elements of the inclusions in the surface of the specimen.

7 Claims, 25 Drawing Figures

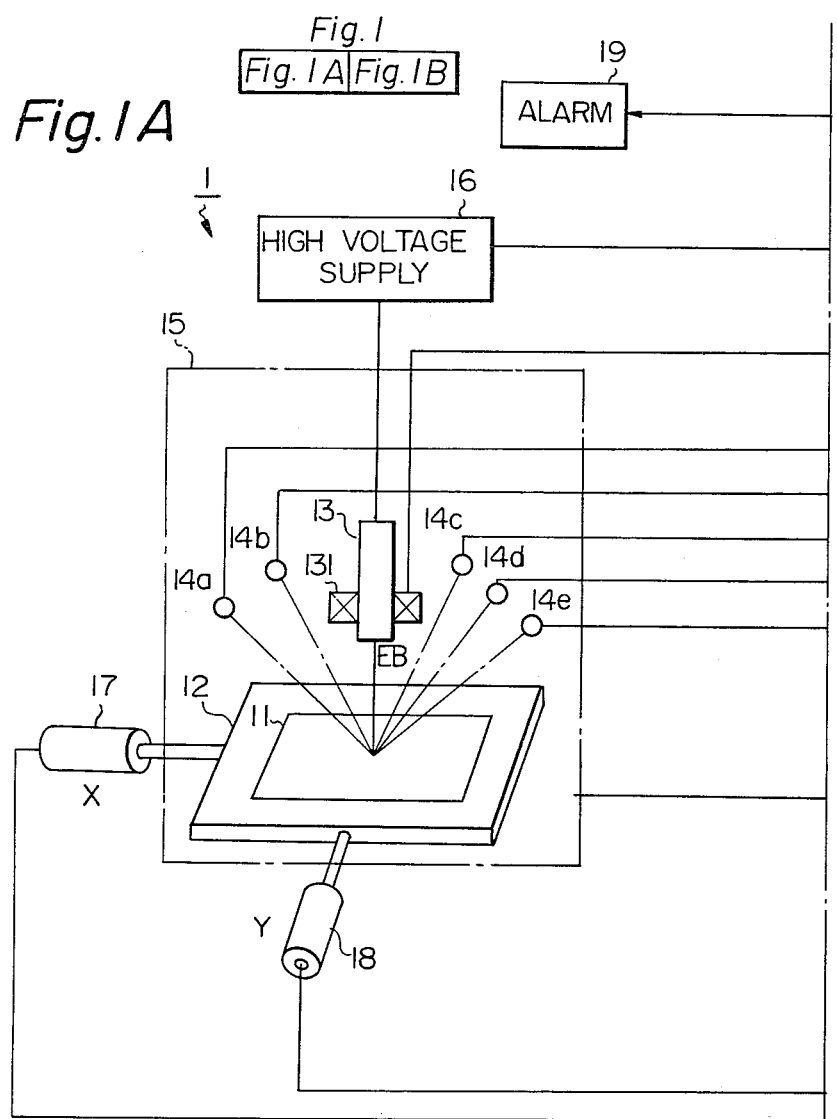

| P | B | J |
|---|---|---|
| POSITION SIGNAL | CRACK SIGNAL | X-RAY SIGNAL |

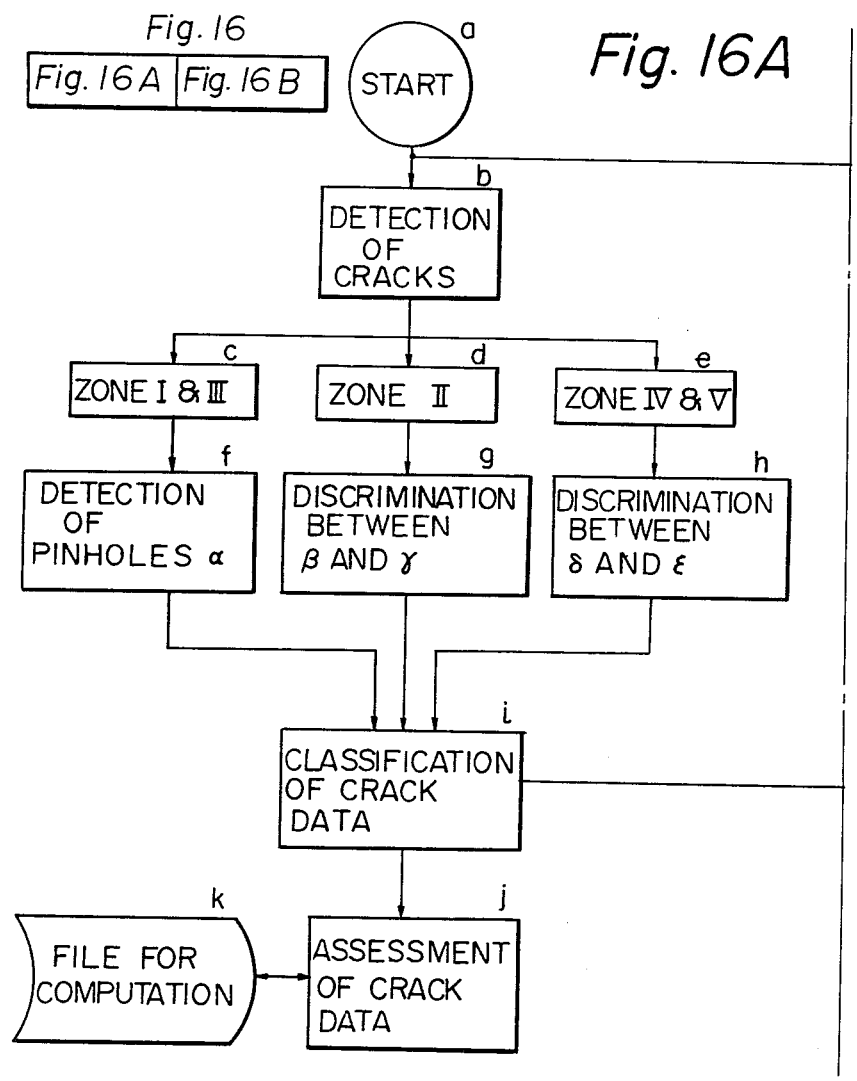

METHOD FOR MEASUREMENT OF DISTRIBUTION OF INCLUSIONS IN A SLAB BY ELECTRON BEAM IRRADIATION

TECHNICAL FIELD

The present invention relates to a method for the measurement of the distribution of the inclusions in a slab by using an electron beam. The method of the present invention is applicable to the investigation of the property of steel in the form of a slab in which such inclusions as sulfur, aluminum, manganese or the like are distributed two-dimensionally.

BACKGROUND OF THE INVENTION

It has been known to use a sulfur print testing method to detect the segregation and the distribution of sulfur in steel. In that sulfur print testing method, photographic paper soaked with a sulfuric acid solution is attached to the surface to be tested, such as a cross-section of a slab. However, this method involves a problem in that it requires a considerable amount of time to polish the surface to be tested, because a very smooth surface is required in this method. Also, it is a problem in this method that only sulfur is mainly detected, and no inclusions other than sulfur can be directly detected. Although, formerly, aluminum and manganese could be indirectly detected using the result of the detection of alumina ($Al_2O_3$) and manganese detected by the sulfur print testing method, difficulties have been increased in such indirect detection because the concentration of sulfur in steel has been reduced recently.

It has also been known to use the X-ray micro analyser method for the measurement of the inclusions in a specimen, by which method various inclusions present on the surface to be tested are directly detected. In this method, an electron beam having a very small diameter, for example, with a diameter between approximately 1 $\mu m$ and 10 $\mu m$, is irradiated onto the surface to be tested. The X-rays emitted from the inclusions due to the irradiation of the electron beam are detected, so that the elements and the quantities of the inclusions are determined two-dimensionally. However, this method includes a problem in that the detector is located lower than the specimen to be tested, due to the use of an analyzing crystal having a curved surface, and hence, the size of the specimen is limited, so that only specimens having a size smaller than 20×20 $mm^2$ can be used. In such specimens of small size, only a small length, on the order of a few millimeter, is scanned mechanically and cannot be scanned by electron beam due to use of an analytical crystal having a curved surface. Accordingly, in this method, such a wide area detection as in the case of the sulfur print testing method cannot be effected. Also, again it is a problem in this method that it requires a considerably amount of time to polish the surface to be tested, because a smoothness which is similar to the smoothness required for specimens for an electron microscope is required for a specimen for this method.

The present invention has been proposed in order to solve the above described problems in the prior art methods.

SUMMARY OF THE INVENTION

It is the main object of the present invention to provide a method for the measurement of the distribution of the inclusions and segregation in a slab by using an electron beam in which less time is required for polishing the surface to be tested of the cross-section of a slab than in the case of the sulfur print testing method, the detection of the distribution of the inclusions and segregation in the area as broad as in the case of the sulfur print testing method can be effected and the direct detection of the distribution of inclusions other than sulfur can be effected whether sulfur exists or not.

According to the present invention, a method for the measurement of the distribution of the inclusions in a slab by detecting the characteristic X-rays emitted by the elements of the inclusions due to the irradiation of an electron beam is provided, which method is characterized in that it comprises the steps of: irradiating an electron beam having a cross-section with a diameter between 0.1 mm and 10 mm onto a specimen of a slab on a table in an evacuated chamber; effecting a spectrum analysis of the X-rays emitted from the surface of the specimen due to the irradiation of the electron beam by using flat surface analyzing crystals; moving the table relative to the electron beam for varying two-dimensionally the position of the electron beam irradiation on the surface of the specimen, and; obtaining the data of the two-dimensional distribution of the elements of the inclusions in the surface of the specimen.

According to a modified embodiment of the present invention, a method for the measurement of the distribution of the inclusions in a slab including cracks on the surface thereof by detecting the characteristic X-rays emitted by the elements of the inclusions due to the irradiation of an electron beam is provided, which method is characterized in that it comprises the steps of: irradiating an electron beam having a cross-section with a diameter between 0.1 mm and 10 mm onto a specimen of a slab, having rough surface, on a table in an evacuated chamber; effecting a spectrum analysis of the X-rays emitted from the surface of the specimen due to the irradiation of the electron beam by using flat surface analyzing crystals; moving the table relative to the electron beam for two-dimensionally varying the position of the electron beam irradiation on the surface of the specimen, and; obtaining the data of the two-dimensional distribution of the elements of the inclusions and the cracks in the surface of the specimen.

BRIEF DESCRIPTION OF THE DRAWINGS

FIGS. 1A–B illustrates a device for the measurement of the inclusions and cracks in a slab used in an embodiment of the present invention;

PREFERRED EMBODIMENTS OF THE INVENTION

Figure 1B:
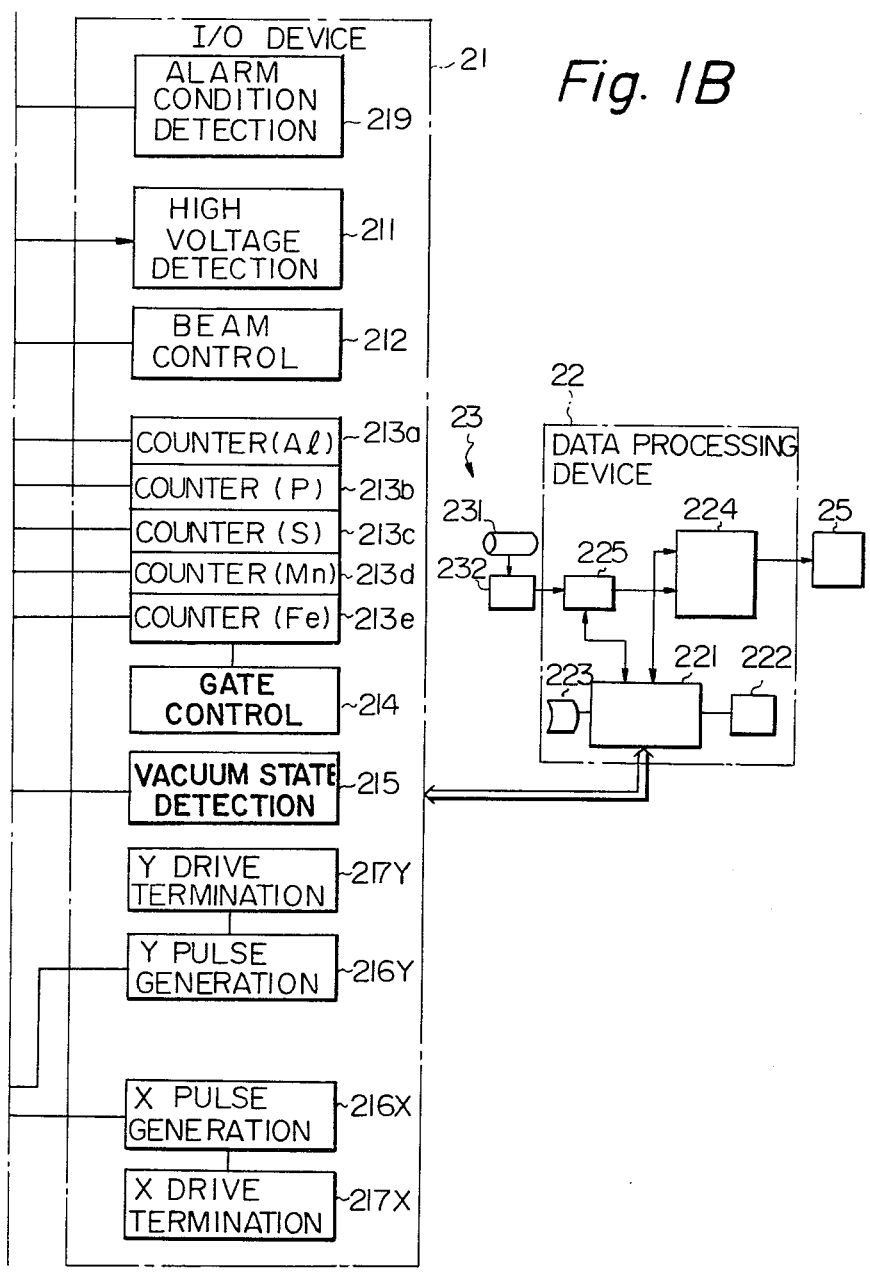

A device for the measurement of the distribution of the inclusions in a slab is illustrated in FIG. 1. In a evacuated chamber 15 of a detector 1, a specimen 11 on a table 12 is irradiated by an electron beam EB emitted from an electron gun 13. The table 12 is driven in the X-axis direction and in the Y-axis direction by an X-axis pulses motor 17 and a Y-axis pulse motor 18. The specimen 11 is obtained by cutting a slab of steel produced by continuous casting (CC). The lengths along the X- and Y-axis of the specimen 11 are, for example, 2 m and 30 cm, respectively. It is also possible to use a specimen 2 m×15 cm or 1 m×30 cm, which is one half of the size of the specimen 2 m×30 cm, or a specimen 1 m×15 cm, which is one quarter of the size of the specimen 2 m×30 cm. The electron beam EB having a cross-section with diameter between approximately 0.1 mm and 10 mm is irradiated either intermittently or continuously onto the specimen 11.

X-ray spectrometers 14a, 14b, 14c 14d and 14e are provided in the evacuated chamber 15 to receive the characteristic X-rays produced from inclusions and iron in the specimen due to the irradiation of the electron beam onto the inclusions and iron. The X-ray spectrometers transduce the received characteristic X-rays to corresponding electrical signals in which one pulse of the electrical signal corresponds to one X-ray quantum.

The detector 1 is connected to an input/output device 21 which is connected to a data processing device 22. In the input/output device 21, there are provided a high voltage detection unit 211, a beam control unit 212, pulse counters 213a through 213e, a gate control unit 214 for the pulse counters 213a through 213e, a vacuum condition detection unit 215, X-axis and Y-axis pulse generation units 216X and 216Y, X-axis and Y-axis drive termination units 217X and 217Y, and an alarm condition detection unit 219.

The high voltage detection unit 211 receives a signal from the high voltage supply circuit 16 for detecting the high voltage supplied to the electron gun 13. The beam control unit 212 controls the diameter of the electron beam EB. The vacuum state detection unit 215 detects the vacuum state of the evacuated chamber 15. The pulse counters 213a through 213e count the output pulse produced from the X-ray spectrometers 14a, 14b, 14c, 14d and 14e. The counting periods of the pulse counters 213a through 213e are controlled by the gate control unit 214 for determining the start and the termination of the counting of the pulse counters 213a through 213e. The X-axis and Y-axis pulse generation units 216X and 216Y supply the driving pulses to the X-axis and Y-axis pulse motors 17 and 18, respectively, for varying the relative position between the specimen 11 and the electron beam EB. Although, in the embodiment of FIG. 1, the movements of the table 12 in both X-axis and Y-axis directions are driven mechanically by the pulse motors, it is possible to replace either of the X-axis or Y-axis movements by electron beam EB with a span of approximately 30 cm. The alarm condition detection unit 219 supplies an alarm signal to an alarm device 19, such as an alarm lamp.

The input/output device 21 is connected to the data processing device 22 which receives the detected data from the detector 1 through the input/output device 21, stores and processes the received data, displays the result of the processing and supplies control signals to the detector 1 through the input/output device 21. The data processing device 22 comprises a central processing unit 221, a controlling console 222, a disc picture file 223, memory planes for picture and processing unit 224 and a display unit 25. A scanning system 23 including a drum scanner 231 and an analog-to-digital convertor 232 is connected to the data processing device 22.

Figure 2:
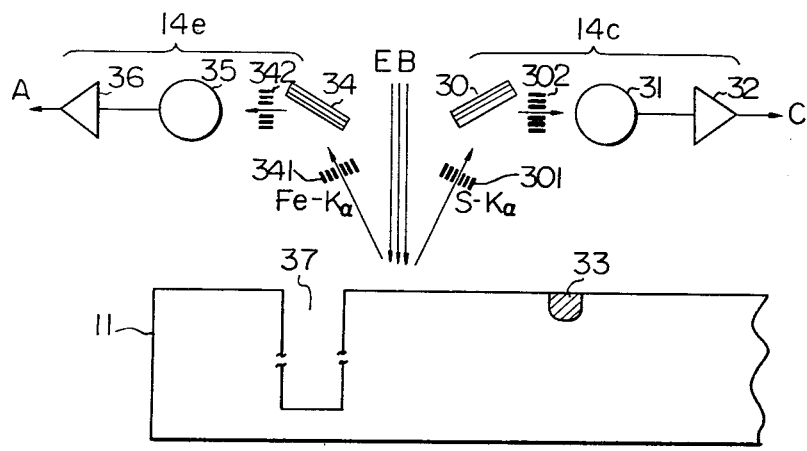
FIGS. 2, 3 and 4 illustrate an example of the device and the process for the measurement of the elements of the inclusions and the cracks used in the device of FIG. 1.
Figure 3:
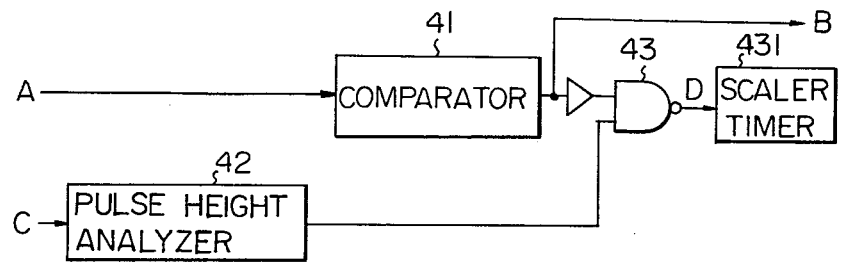
Figure 4:
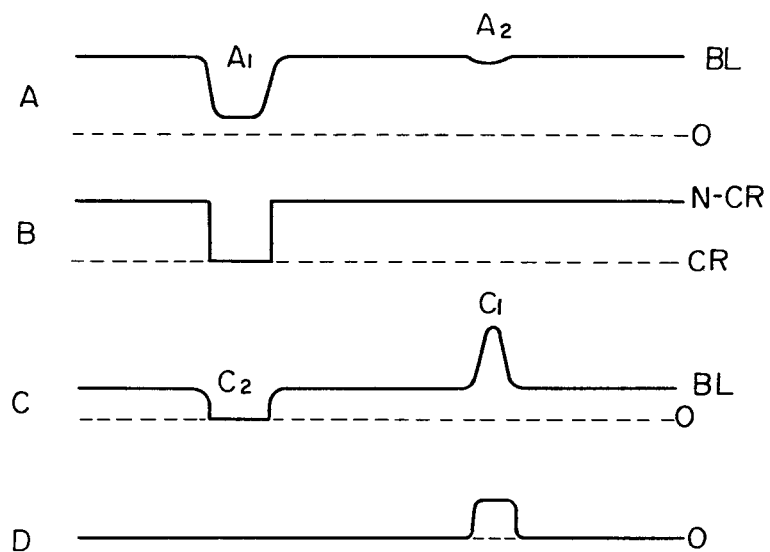

The process of the measurement of the characteristic X-rays produced by the specimen 11 due to the irradiation of the electron beam EB is illustrated in FIGS. 2, 3 and 4. Only two of the X-ray spectrometers 14c and 14e among the set of X-ray spectrometers 14a through 14e which are located in front of the specimen 11 are illustrated in FIG. 2. The X-ray spectrometer 14c is used for the detection of the characteristic X-ray S-K$\alpha$. The X-ray spectrometer 14e is used for the detection of the characteristic X-ray Fe-K$\alpha$. Although not shown in FIG. 2, the X-ray spectrometers 14a, 14b, 14d are used for the detection of the characteristic X-rays Al-K$\alpha$, P-K$\alpha$ and Mn-K$\alpha$, respectively. The characteristic X-ray after passing through a collimator 301 reflected from the surface of a flat surface analyzing crystal 30 passes through a collimator 302 and is received by a X-ray detector 31 which transduces the received characteristic X-ray into an electrical signal which is supplied to an amplifier 32 to produce an output signal C. It should be noted that an analyzing crystal having a curved surface which is used for an X-ray microanalyzers system cannot be used for the device of FIG. 2. This is because a very severe condition of light focusing is required for the system using an analyzing crystal having a curved surface and such very severe condition cannot be applied to the device of FIG. 2 which deals with a specimen of large size.

In the device of FIG. 2, an inclusion 33 in the specimen 11 is excited by the irradiated electron beam EB and produces a characteristic X-ray corresponding to the elements of the inclusion, such as aluminum, phosphorus, sulfur or manganese. These characteristic X-rays are detected by the X-ray spectrometers 14a, 14b, 14c and 14d. The portion of the surface of the specimen 11 other than the portion of inclusion 33 is also excited by the irradiated electron beam EB and produces the characteristic X-ray corresponding to iron. The characteristic X-ray from this portion is detected by the X-ray spectrometer 14e. The characteristic X-ray after passing through a collimator 341 reflected from the surface of a flat surface analyzing crystal 34 passes through a collimator 342 and is received by a X-ray detector 35 which transduces the received characteristic X-ray into an electric signal which is supplied to an amplifier 36 to produce an output signal A. If there is a crack 37 with a size of approximately 1 mm on the surface of the specimen 11, the values of both output signals C and A are reduced below a background level BL.

A circuit for dealing with the output signals of the device of FIG. 2 is illustrated in FIG. 3. The output signals A and C are applied to comparator 41 and pulse height analyzer 42, respectively. The output signal A is applied to the comparator 41 which produces a crack detection signal B. The outputs of both the comparator 41 and the pulse height analyzer 42 are applied to the inputs of a NAND gate 43 which produces a signal D which is applied to a scaler timer 431. The changes in the signals A, B, C and D are illustrated in FIG. 4. The signal A falls greatly below the background level BL as $A_1$ corresponding to the crack 37 and falls slightly below the background level BL as $A_2$ corresponding to the inclusion 33. As this slight fall $A_2$ is remedied by a wave form shaping, the signal B having a level N-CR indicating non-crack state and a level CR indicating crack state is obtained. The signal C falls below the background level BL as $C_2$ corresponding to the crack 37 and rises over the background level BL as $C_1$ corresponding to the inclusion 33. Due to the production of the signal D at the output of the NAND gate 43, the fall $C_2$ is not supplied to the scaler timer 431 and only the rise $C_1$ is supplied to the scaler timer 431.

Figure 5:
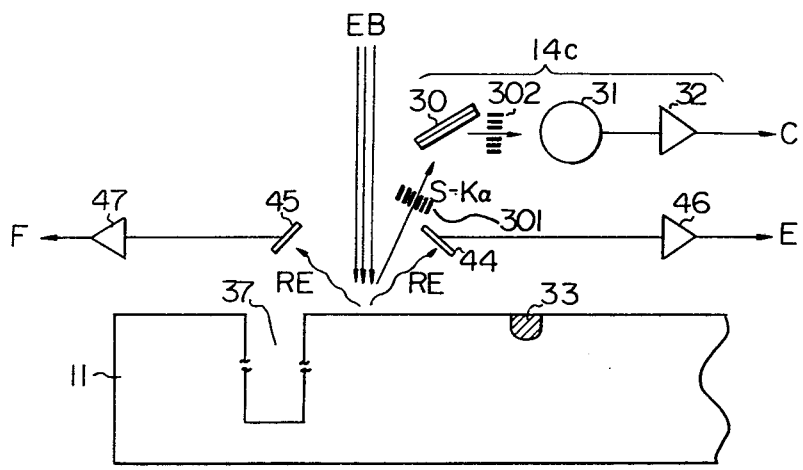
FIGS. 5 and 6 illustrate another example of the device and the process for the measurement of the elements of the inclusions and the cracks used in the device of FIG. 1.
Figure 6:
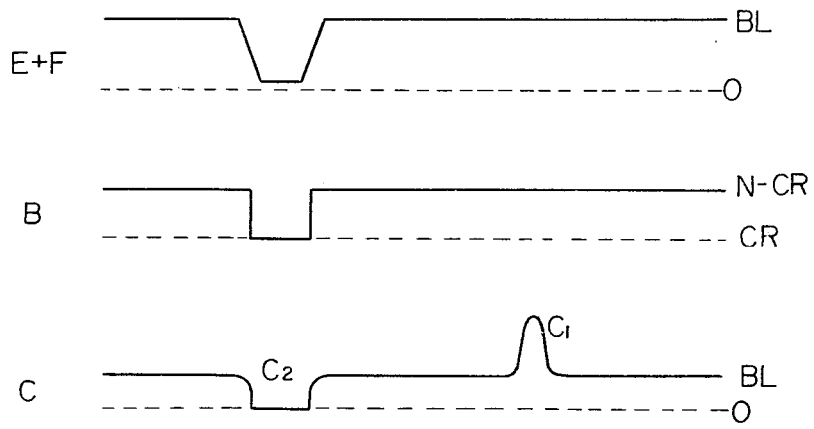

A modification of the process of FIGS. 2, 3 and 4 is illustrated in FIGS. 5 and 6. In the device of FIG. 5, the crack 37 is detected by using electron detectors 44 and 45 which detect reflected electrons RE caused by the reflection of the irradiated electron beam EB at the surface of the specimen 11. Usually approximately 30% of the irradiated electrons are reflected at the surface of the specimen 11. Output signals of the electron detectors 44 and 45 are amplified by amplifiers 46 and 47, the outputs of which are summed to produce a signal "E+F" as illustrated in FIG. 6. Accordingly, the signal B indicating the crack by the level CR is obtained from the signal "E+F".

Figure 7:
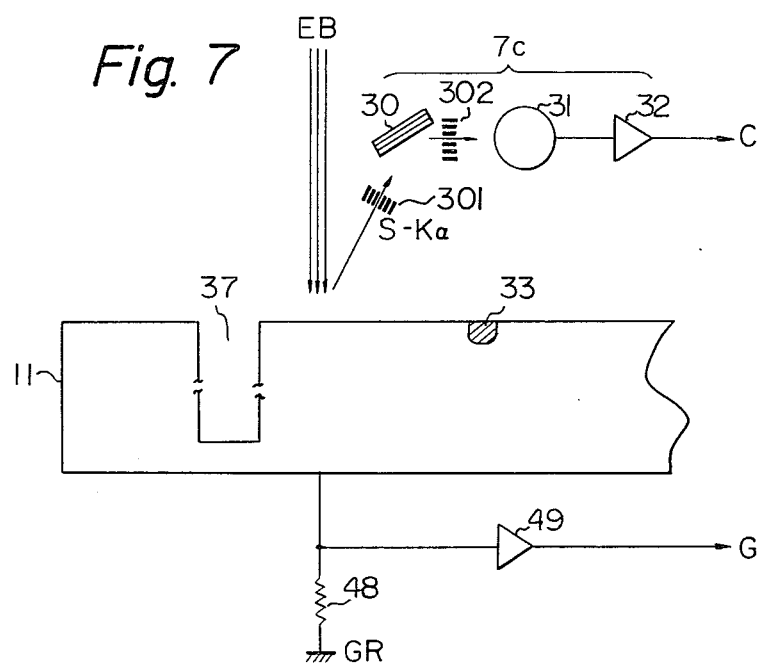
FIGS. 7 and 8, and FIGS. 9 and 10 are two further examples of the device and process for the measurement of the elements of the inclusions and the cracks used in the device of FIG. 1.
Figure 8:
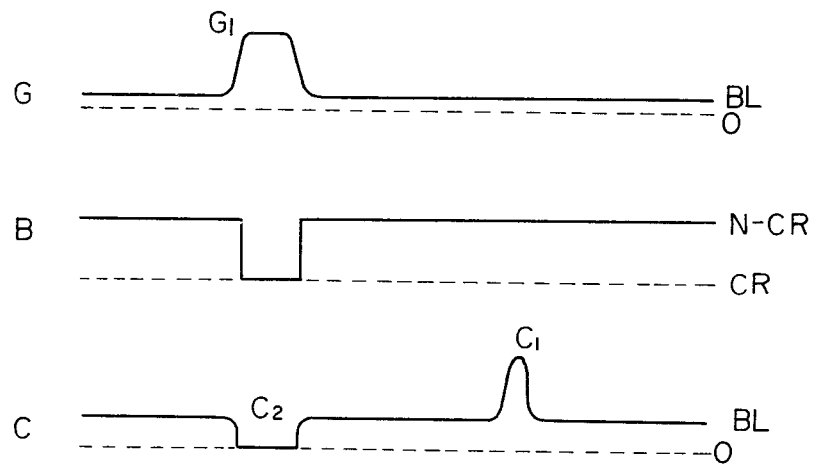

Another modification of the process of FIGS. 2, 3 and 4 is illustrated in FIGS. 7 and 8. In the device of FIG. 7, the crack 37 is detected by using a resistor 48 for detecting the current passing through the specimen 11 to ground GR due to the absorption of a portion of the irradiated electrons EB by the specimen 11. The specimen 11 is insulated from ground except for the electrical connection through the resistor 48. The voltage across the resistor 48 is amplified by an amplifier 49 to produce a signal G. The signal G rises to a level $G_1$ (FIG. 8) corresponding to the crack 37. The signal B indicating the crack by the level CR is obtained from the signal G as illustrated in FIG. 8.

Figure 9:
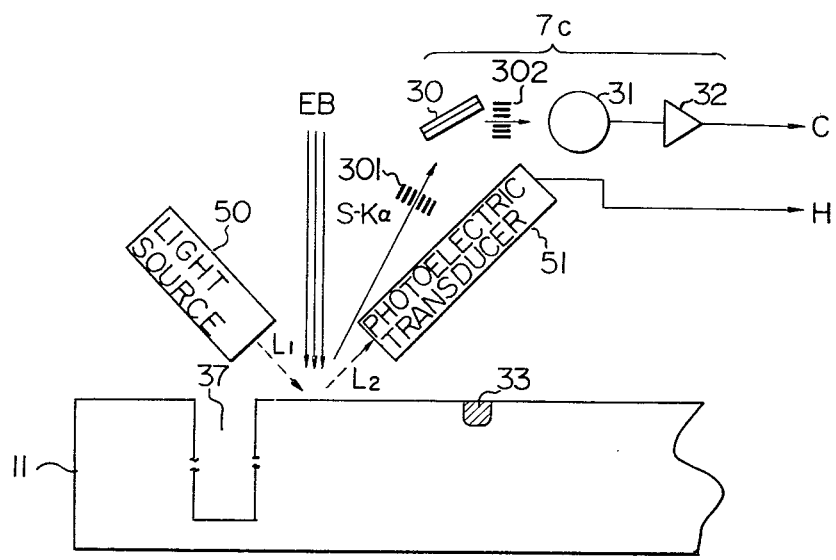
Figure 10:
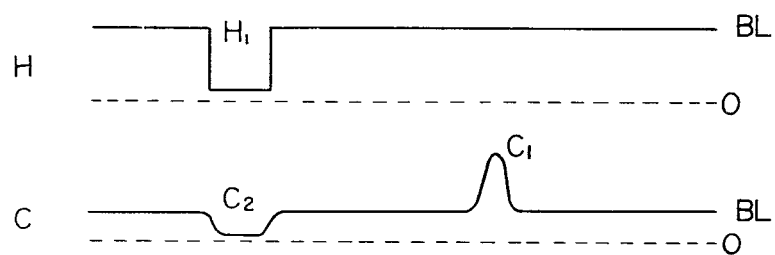

Still another modification of the process of FIGS. 2, 3 and 4 is illustrated in FIGS. 9 and 10. In the device of FIG. 9, the crack 37 is detected by means of a reflection of light, i.e. laser beam or infrared beam, in place of the reflection or absorption of the electron beam in FIGS. 2, 5 and 7. A light beam $L_1$ which is emitted from a light source 50 and reflected $L_2$ by the surface of the specimen 11 is received and transduced into electric signal by a photoelectric transducer 51 to produce an output signal H. The signal H falls to a level $H_1$ (FIG. 10) corresponding to the crack 37. Accordingly, the signal H can be used as the signal for indicating the crack as is the signal B in FIGS. 2, 5 and 7.

Figure 11:
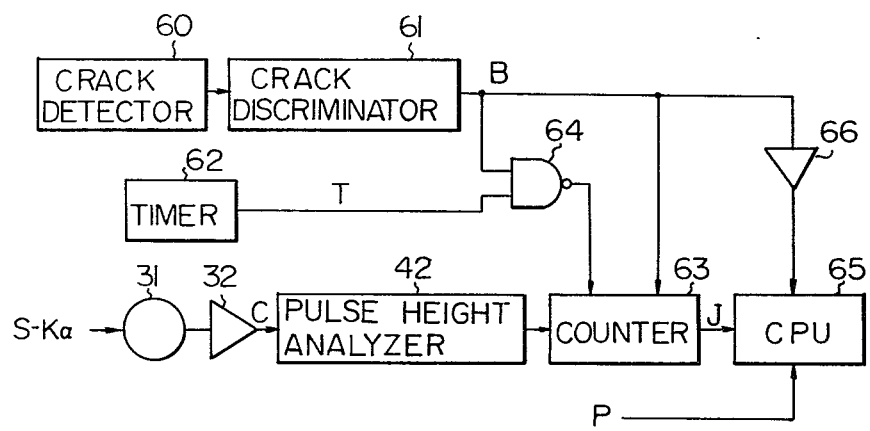
FIG. 11 illustrates a modification of the circuit of FIG. 3.
Figures 12A, 12B:
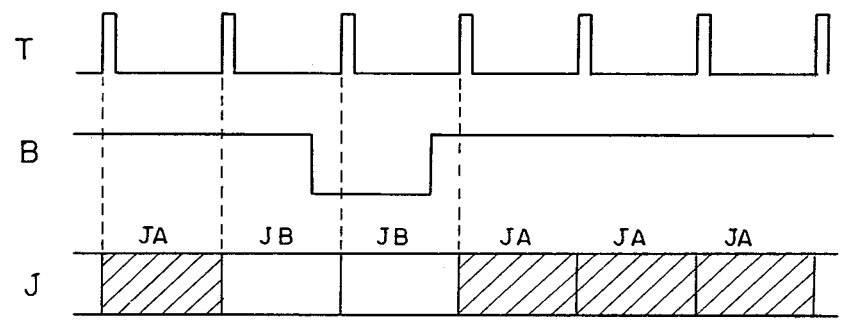
FIGS. 12A and 12B illustrate an operation of the circuit of FIG. 11.

A modification of the circuit of FIG. 3 is illustrated in FIG. 11. The manner of operation of the circuit of FIG. 11 is illustrated in FIGS. 12A and 12B. A crack detector 60 and a crack discriminating unit 61 correspond to the means for detecting and determining the crack, respectively, in the devices of FIGS. 2, 5, 7 and 9. The crack indicating signal B and a timing signal T produced by a timer 62 are supplied to the inputs of a NAND gate 64. The signal B is supplied to a counter 63 and to a buffer amplifier 66, the output of which is supplied to a central processing unit 65. The characteristic X-ray S-K$\alpha$ is converted by the X-ray detector 31 into an electric signal which is amplified by the amplifier 32 to produce the signal C. The signal C is supplied to the input of the pulse height analyzer 42, the output of which is supplied to the counter 63. The counter 63 receives the output signal of the NAND gate 64, the signal B and the output signal of the pulse height analyzer 42. The signal B supplied to the counter 63 clears the count of the counter 63.

The pattern of a signal J illustrated in FIG. 12A consist of the portion JA in which the signal J indicates the count of the detected characteristic X-ray signals and the portion JB in which the count of the counter 63 is cleared and the counting of the counter 63 is stopped. The signal J, the amplified signal B and a position signal P, which indicates the position at which the signal J or the signal B are obtained, are supplied to the central processing unit 65. In the memory device controlled by the central processing unit 65, a set of data consisting of the position signal P, the crack signal B and the characteristic X-ray signal J is stored with the pattern illustrated in FIG. 12B. The position signal P is the signal of the X-axis and Y-axis positions of the table 12 illustrated in FIG. 1. A saw-toothed signal is used for relative motion between the electron beam EB and the table 12 in order to vary the X-axis and Y-axis positions of the table 12 relative to the electron beam EB. The position signal P can also be used for the driving signal of the timer 62 for synchronization.

Figure 13:
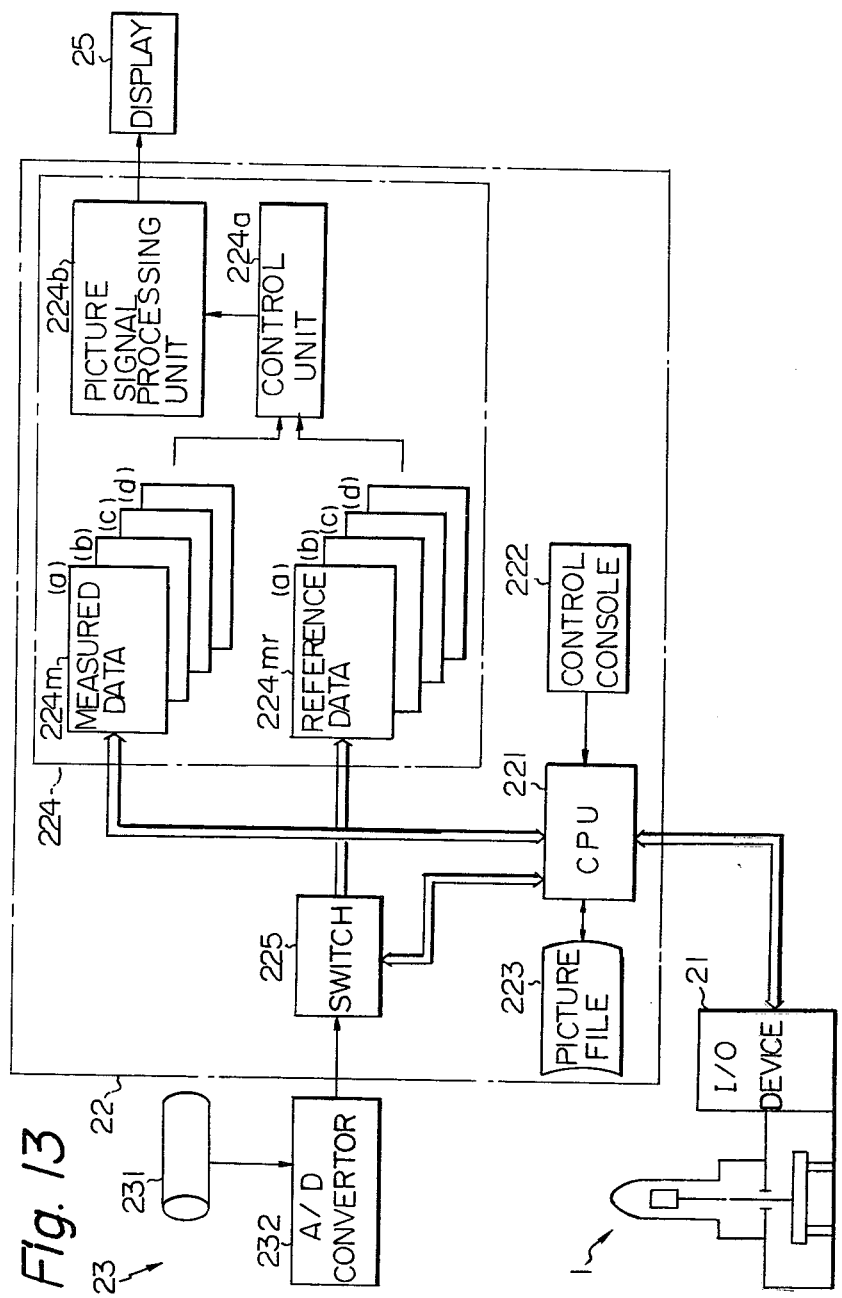
FIG. 13 illustrates the details of the data processing device in the device of FIG. 1.

The details of the data processing device 22 in the device of FIG. 1 are illustrated in FIG. 13. The data from the input/output device 21 is sent to and stored in memory planes for measured data 224m for the measured picture data through the central processing unit 221. The reference picture data obtained from the picture file on the disc 223 or from the scanning system 23, comprising the drum scanner 231 and the analog-to-digital converter 232, is sent to and stored in memory planes for reference data 224mr for the reference picture data. The known picture of sulfur print test photographic paper is scanned on the drum scanner 231. The data from the memory planes 224m for the measured picture data and the data from the memory planes 224mr for the reference picture data are switched, composed, superposed, or otherwise treated by a control unit 224a which supplies an output signal to a color picture signal processing unit 224b which supplies a display signal to the display unit 25. Observing the picture displayed on the display unit 25, the operator of the device can identify which reference picture data corresponds to the measured picture data. Such identification can also be effected automatically by using an appropriate process of processing logic.

Figure 14:
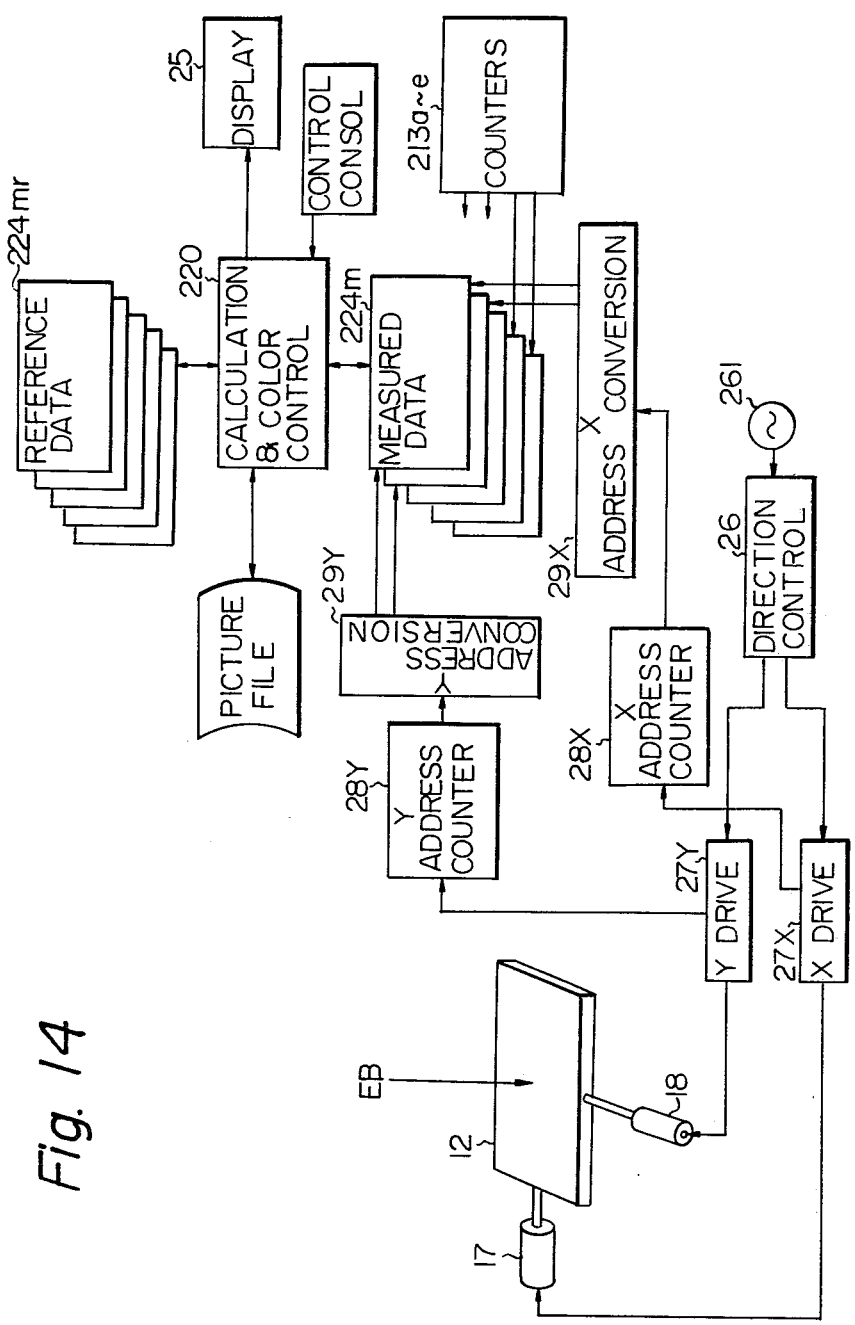
FIG. 14 illustrates an operation carried out by the device of FIG. 1.

The operation of the device of FIG. 1 for effecting the correspondence between the address of the measured picture data stored in memory planes for measured data 224m and the position of irradiation of the electron beam EB on the specimen 11 is illustrated in FIG. 14. Pulses produced by a clock generator 261 are supplied to X-axis and Y-axis driving units 27X and 27Y through a direction control unit 26. The X-axis and Y-axis driving units 27X and 27Y, which include the X-axis and Y-axis pulse generation units 216X and 216Y, respectively, drive the pulse motors 17 and 18, respectively. Simultaneously the number of the driving pulses is counted by an X address counter 28X and a Y address counter 28Y. The contents of the counters 28X and 28Y indicate the abscissa and the ordinate of the point of the irradiation of the electron beam EB, because the above mentioned driving pulses correspond to the distances from the origin of the axis of coordinates X, Y. X-axis and Y-axis address conversion units 29X and 29Y convert the signals from the X and Y address conversion counters 28X and 28Y, respectively, into codes which are suitable for retrieval of the data stored in the memory planes 224m for the measured picture data. These codes correspond to the position signal P illustrated in FIG. 12B.

Figure 15:
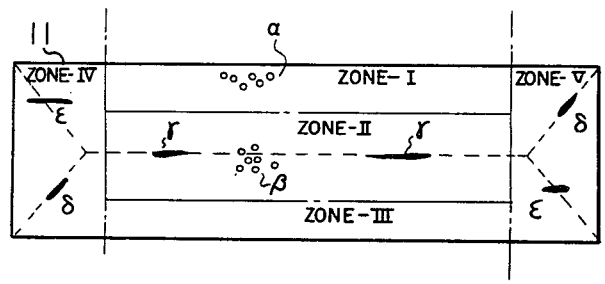
FIG. 15 illustrates a pattern of a specimen applicable to the device of FIG. 1.

Signals representing the analyzed elements Al, P, S, Mn or the like produced by the pulse counters 213a through 213e are supplied to the memory planes 224m for the measured picture data. These signals correspond to the characteristic X-ray signal J illustrated in FIGS. 12A and 12B. Simultaneously, the crack indicating signal B and the position signal P are also written in the memory planes 224m as addresses. A calculation and color control unit 220 corresponds to the central processing unit 221, the control unit 224a and the colored picture signal processing unit 224b illustrated in FIG. 13. A typical pattern of a cross-section of a slab of steel having cracks produced by continuous casting (CC), is illustrated in FIG. 15. The cross-section of the slab is divided into five zones: I, II, III, IV and V. In zone-II, in which a so-called sulfur band is formed, an alumina cluster $\beta$ and lateral cracks $\gamma$ exist. In zone I, which is located above the zone II, in FIG. 15, pinholes $\alpha$ exist. In zones IV and V, which are located symmetrically on the left and right sides of zone II, in FIG. 15, oblique cracks $\delta$ and lateral cracks $\epsilon$ exist. In accordance with the embodiment of the method of the present invention, the cracks $\gamma$, $\delta$ and $\epsilon$ and the pinholes $\alpha$ are detected simultaneously with the detection of the elements of the inclusions.

Figure 16B:
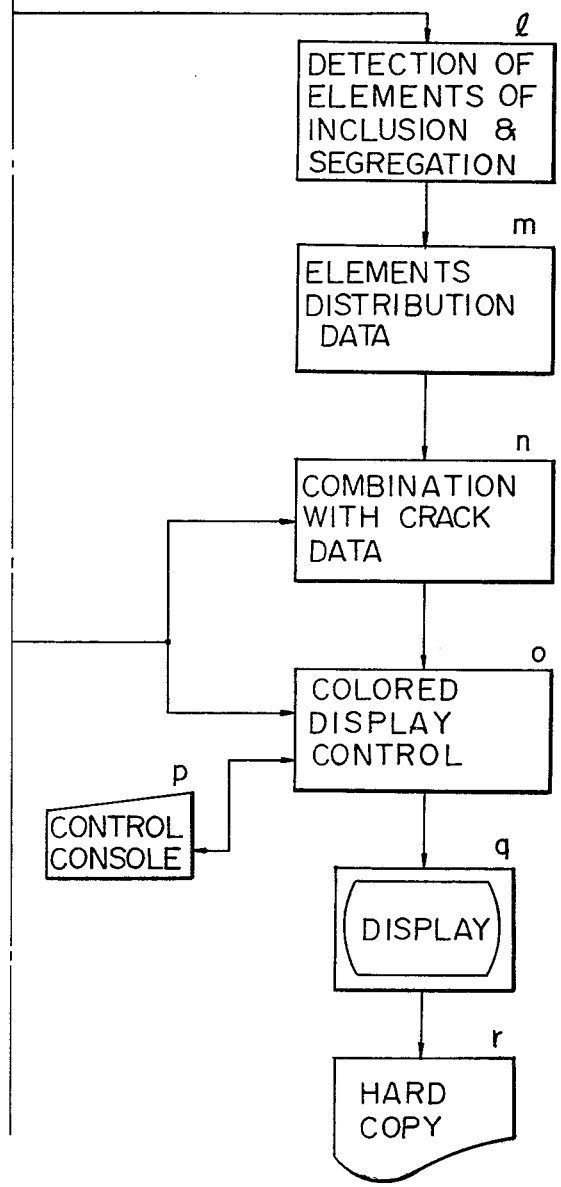
FIG. 16 illustrates a flow chart for the operation carried out by the data processing device in the device of FIG. 1.
Figure 19A:
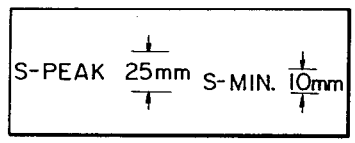
FIGS. 19A, 19B, 19C and 19D illustrate examples of the manner of display in the device of FIG. 1.
Figure 19B:
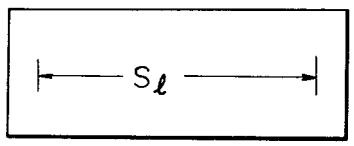
Figure 19C:
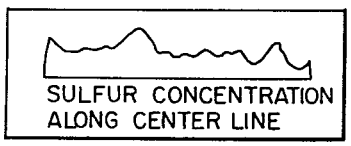
Figure 19D:
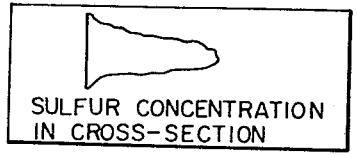

An example of the flow chart of the logic of the process achieved by the data processing device 22 is illustrated in FIG. 16. Following the start (a) two main treatments, i.e. detection of cracks (b) and detection of the elements of the inclusion (l) are carried out. The detection of cracks (b) is followed by the treatment for the zones I and III (c), the treatment for the zone II (d) and the treatment for the zones IV and V (e). Following the treatment (c), a treatment (f) is effected in which the pinholes $\alpha$ are detected. Following the treatment (d), a treatment (g) is effected in which the descrimination between the types $\beta$ and $\gamma$ of cracks is carried out. Following the treatment (e), a treatment (h) is effected in which the discrimination between the direction of the cracks $\delta$ and $\epsilon$ is carried out. Then, the data of the cracks obtained in the treatments (f), (g) and (h) are classified in a treatment (i), and the resulting data undergoes an assessment of the cracks by a treatment (j) and afterwards is stored in a file (k) for computation. The data obtained in the detection of the elements of the inclusion (l) is treated in a treatment (m) in which the data of the distribution of the elements is obtained. Then, a treatment (n) combines the data of the distribution of elements from the treatment (m) and the data of the cracks from the treatment (i) and produces colored picture display data which is applied to a colored display control (o). Data produced in the colored display control (o) is displayed by a display (q) and, if necessary, is recorded in hard copy (r) form. The colored display control (o) is connected to a control consol (p).

Figure 17:
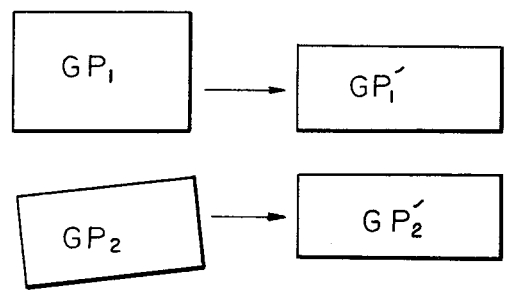
FIGS. 17 and 18 illustrate an example of the calculating and color controlling operation of the device of FIG. 1.
Figure 18:
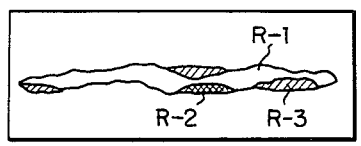

An example of the process effected in the calculation and color control unit 220 of FIG. 14 is illustrated in FIGS. 17 and 18. Due to the process of calculation conducted in the unit 220, coincidence between the positions in the memory planes 224m and the positions in the memory planes 224mr is achieved. Assume that $GP_1$ is the picture pattern stored in the memory planes 224m for the measured picture data and $GP_2$ is the picture pattern stored in the memory planes 224mr for the reference picture data. The reduced scales and the angular directions of $GP_1$ and $GP_2$ are not the same. As a result of the above described calculation conducted in the unit 220, the picture pattern $GP_1$ is converted into a modified picture pattern $GP_1'$ and the picture pattern $GP_2$ is converted into a modified picture pattern $GP_2'$. The calculation is conducted so that the geometrical scales of $GP_1$ and $GP_2$ are made identical, the horizontal, vertical and angular positions of $GP_1$ and $GP_2$ are modified and the pattern of $GP_1$ can be placed coincidentally on the pattern of $GP_2$. The modified picture patterns $GP_1'$ and $GP_2'$ can be superposed without discrepancy in the positions of the picture patterns. Referring to FIG. 18, which illustrates a display of the display device 25, due to the control conducted in the unit 220, a first region (R-1) of the picture pattern, in which the value of the measured picture data is equal to that of the reference picture data, a second region (R-2) of the picture pattern, in which the value of the measured picture data is greater than that of the reference picture data, and a third region (R-3) of the picture pattern, in which the value of the measured picture data is smaller than that of the reference picture data, are displayed in different colors on the display device 25. If, due to the switching by the control of the unit 220, the data stored in the memory planes 224m for the measured picture data is supplied to the display device 25, the measured picture pattern itself is displayed on the display device 25. The display on the display device 25 is effected for each of the elements, such as aluminum, phosphorus, sulfur, manganese or the like.

Examples of the manner of display other than the manner illustrated in FIG. 18 are illustrated in FIGS. 19A, 19B, 19C and 19D. In the manner illustrated in FIG. 19A, the peak value (S-PEAK) and the minimum value (S-MIN) of the sulfur band in the specimen are displayed. In the manner illustrated in FIG. 19B, the length of the sulfur band Sl in the specimen is displayed. In the manner illustrated in FIG. 19C, the distribution of the concentration of sulfur along the center line of the sulfur band in the specimen is displayed. In the manner illustrated in FIG. 19D, the distribution of the concentration of sulfur in the direction perpendicular to the center line of the sulfur band in the specimen is displayed. It is also possible to display the total area of the sulfur band in the specimen, although that not illustrated in the drawings. Furthermore, it is possible to achieve the automatic classification of the specimens in accordance with the difference in the qualities of the specimen from the view points of the segregation and distribution of the elements of the inclusion and the cracks, using the picture data displayed on the display device.

As a result of an investigation conducted by the inventors, it has been confirmed that the preferable range of the diameter of the cross-section of the electron beam is between 0.1 mm and 10 mm. This is because, if the diameter is smaller than 0.1 mm, the number of scanning lines is increased, and hence, the amount of data is increased, which prevents the present invention from being practically used, and; if the diameter is larger than 10 mm, the resolving power of an X-ray spectrometer is insufficient to obtain reliable data. It has been found that, due to the relatively large diameter of the electron beam used, a considerably large area of the specimen, corresponding to the area involved in the sulfur print testing method, to which area it has been substantially impossible to apply the prior art X-ray analysis, can be measured in a considerably short time in accordance with the present invention. Because the electron beam of such a larged diameter is used, no such smoothness of the surface of the specimen as is required for the sulfur print testing method is required in accordance with the present invention. For example, only one process of rough surface polishing by a grinder is sufficient for polishing the specimen in accordance with the present invention, so that the polishing time is reduced to approximately one tenth of the polishing time required for the sulfur print testing method.

We claim:

1. A method for the measurement of the distribution of the inclusion in a slab by detecting the characteristic X-rays emitted by the elements of the inclusions due to the irradiation of an electron beam, characterized in that said method comprises the steps of:
    irradiating an electron beam having a cross-section with a diameter between 0.1 mm and 10 mm onto a specimen of a slab on a table in an evacuated chamber;
    effecting a spectrum analysis of the X-rays emitted from the surface of the specimen due to the irradiation of the electron beam by using flat surface analyzing crystals;
    moving the table relative to the electron beam for two-dimensionally varying the position of the electron beam irradiation on the surface of the specimen, and;
    obtaining the data of the two-dimensional distribution of the elements of the inclusions in the surface of the specimen.

2. A method as defined in claim 1, wherein said specimen of a slab has a rough surface.

3. A method for the measurement of the distribution of the inclusions in a slab including cracks on the surface thereof by detecting the characteristic X-rays omitted by the elements of the inclusions due to the irradiation of an electron beam, characterized in that said method comprises the steps of:
    irradiating an electron beam having a cross-section with a diameter between 0.1 mm and 10 mm onto a specimen of a slab, having rough surface, on a table in an evacuated chamber;
    effecting a spectrum analysis of the X-rays emitted from the surface of the specimen due to the irradiation of the electron beam by using flat surface analyzing crystals;
    moving the table relative to the electron beam for two-dimensionally varying the position of the electron beam irradiation on the surface of the specimen, and;
    obtaining the data of the two-dimensional distribution of the elements of the inclusions and the cracks in the surface of the specimen.

4. A method as defined in claim 1, 2 or 3, wherein a specimen of such a large scale as 2 m in length and 30 cm in width is used, said length and width being the same as the length and width of a slab produced by continuous casting.

5. A method as defined in claim 3, wherein the detection of the cracks is effected by the detection of the characteristic X-ray emitted from the element of iron.

6. A method as defined in claim 3, wherein the detection of the cracks is effected by the reflection or the absorption of the portion of the electrons irradiated onto the specimen.

7. A method as defined in claim 3, wherein said method further comprises the steps of:
    simultaneously with said irradiation of the electron beam onto a specimen, irradiating a light beam onto a specimen;
    detecting the light reflected at the surface of the specimen, and;
    producing a signal corresponding to the cracks, whereby data of the two-dimensional distribution of the cracks is obtained.

* * * * *

UNITED STATES PATENT AND TRADEMARK OFFICE
CERTIFICATE OF CORRECTION

PATENT NO. : 4,331,872

DATED : May 25, 1982

INVENTOR(S) : Hiromu Soga; Koichi Kitamura; Tomio Sasaki; Mitsuyoshi Sato; Hiroshi Ishijima It is certified that error appears in the above—identified patent and that said Letters Patent is hereby corrected as shown below:

In item [57] in the Abstract, line 6, change "planar" to
-- flat surface --;
Column 4, line 50, change "a characteristic X-ray" to
-- characteristic X-rays --;
Column 9, line 15, change "larged" to -- large --;
Column 10, Claim 4, line 4, after "width of", insert
-- a cross-section of --.

Signed and Sealed this

First Day of March 1983

[SEAL]

Attest:

GERALD J. MOSSINGHOFF

Attesting Officer     Commissioner of Patents and Trademarks